US008877223B2

(12) United States Patent
Vange et al.

(10) Patent No.: US 8,877,223 B2
(45) Date of Patent: Nov. 4, 2014

(54) DEGRADABLE HYDROPHILIC BLOCK COPOLYMERS WITH IMPROVED BIOCOMPATIBILITY FOR SOFT TISSUE REGENERATION (75) Inventors: Jakob Vange, Helsingør (DK); Khadija Schwach-Abdellaoui, Frederiksberg (DK); Hanne Everland, Bagsværd (DK); Peter Sylvest Nielsen, Værløse (DK); Brian Nielsen, Gørløse (DK); Lene Karin Jespersen, Fredensborg (DK); Lene Feldskov Nielsen, Copenhagen (DK)

(73) Assignee: Coloplast A/S, Humlebaek (DK)

( * ) Notice: Subject to any disclaimer, the term of this patent is extended or adjusted under 35 U.S.C. 154(b) by 1301 days.

(21) Appl. No.: 12/224,891

(22) PCT Filed: Mar. 7, 2007

(86) PCT No.: PCT/DK2007/000115
§ 371 (c)(1),
(2), (4) Date: Sep. 9, 2008

(87) PCT Pub. No.: WO2007/101443
PCT Pub. Date: Sep. 13, 2007

(65) Prior Publication Data
US 2009/0047322 A1 Feb. 19, 2009

(30) Foreign Application Priority Data

Mar. 9, 2006 (DK) .................................. 2006 00337
Sep. 1, 2006 (DK) .................................. 2006 01131
Oct. 26, 2006 (WO) ................. PCT/EP2006/067837

(51) Int. Cl.
*A61F 2/00* (2006.01)
*A61K 9/14* (2006.01)
*B32B 5/14* (2006.01)
*C12N 5/00* (2006.01)
*C12N 5/02* (2006.01)
*C08L 67/00* (2006.01)
*C08G 63/91* (2006.01)
*C08G 63/664* (2006.01)
*A61L 15/26* (2006.01)
*A61L 15/42* (2006.01)
*A61L 27/18* (2006.01)
*A61L 27/56* (2006.01)

(52) U.S. Cl.
CPC .............. *C08G 63/664* (2013.01); *A61L 15/26* (2013.01); *A61L 15/425* (2013.01); *A61L 27/18* (2013.01); *A61L 27/56* (2013.01); *C12N 5/0068* (2013.01); *C08G 2261/126* (2013.01); *C12N 2533/30* (2013.01); *C12N 2533/40* (2013.01)
USPC ........ 424/423; 424/486; 428/308.4; 435/396; 521/138; 525/415

(58) Field of Classification Search
None
See application file for complete search history.

(56) References Cited

U.S. PATENT DOCUMENTS

| 4,716,203 | A | 12/1987 | Casey et al. |
|---|---|---|---|
| 4,820,863 | A * | 4/1989 | Taylor ........................... 560/115 |
| 5,102,983 | A | 4/1992 | Kennedy |
| 5,543,158 | A * | 8/1996 | Gref et al. ..................... 424/501 |
| 5,621,050 | A | 4/1997 | Jarrett et al. |
| 6,201,072 | B1 | 3/2001 | Rathi et al. |
| 6,562,374 | B1 | 5/2003 | Han et al. |
| 2002/0018797 | A1 | 2/2002 | Cui et al. |
| 2004/0076673 | A1 | 4/2004 | Bateman et al. |
| 2007/0014848 | A1 | 1/2007 | Buchholz et al. |

FOREIGN PATENT DOCUMENTS

| CN | 1446841 A | 10/2003 |
|---|---|---|
| EP | 1 234 587 A1 | 8/2002 |
| EP | 1 621 216 A2 | 2/2006 |
| WO | WO 03/000778 A1 | 1/2003 |
| WO | WO 2007/009919 A2 | 1/2007 |

OTHER PUBLICATIONS

Avgoustakis et al. Journal of Controlled Release 2002 79:123-135.*
Huh et al. Drug Delivery Technology 2003 3:1-10.*
Chen et al. Biomaterials 2001 22:2563-2567.*
Chen et al. Materials Science and Engineering C 2001 17:63-69.*
Dressing. (2000). In Collins English Dictionary. Retrieved from http://www.credoreference.com/entry/hcengdict/dressing.*
Jeong et al. Colloids and Surfaces B: Biointerfaces 2000 18:371-379.*
Beletsi et al. International Journal of Pharmaceutics 1999 182:187-197.*
Porjazoska, A., et al., "Synthesis of an ABA Triblock Copolymer of Poly(DL-lactide) and Poly(ethylene glycol) and Blends with Poly(ε-caprolactone) as a Promising Material for Biomedical Application," pp. 119-135.
Beletsi, A., et al., "Biodistribution Properties of Nanparticles based on Mixtures . . . ," International Journal of Pharmaceutics, vol. 298, No. 1, pp. 233-241, Jul. 2005.

(Continued)

Primary Examiner — Juliet Switzer
Assistant Examiner — Caralynne Helm
(74) Attorney, Agent, or Firm — Coloplast Corp., Coloplast A/S; Nick Baumann (57) ABSTRACT The present application discloses biodegradable polymers, to porous and other materials comprising such polymers, and to various medical uses of such materials, including use as a scaffold for supporting cell adhesion or the in-growth for regeneration of tissue. The polymer is of the formula A-O—(CHR$^1$CHR$^2$O)$_n$—B wherein A is a poly(lactide-co-glycolide) residue, the molar ratio of (i) lactide units [—CH(CH$_3$)—COO—] and (ii) glycolide units [—CH$_2$—COO—] in the poly(lactide-co-glycolide) residue being in the range of 80:20 to 10:90, B is either a poly(lactide-co-glycolide) residue or hydrogen, C$_{1-6}$-alkyl or hydroxy protecting groups, one of R$^1$ and R$^2$ is hydrogen or methyl, and the other is hydrogen, n is 10-1000, the molar ratio of (iii) polyalkylene glycol units [—(CHR$^1$CHR$^2$O)—] to the combined amount of (i) lactide units and (ii) glycolide units in the poly(lactide-co-glycolide) residue(s) is at the most 14:86, and the molecular weight of the copolymer is at least 20,000 g/mol.

13 Claims, 5 Drawing Sheets

(56) References Cited

OTHER PUBLICATIONS

Witt, C., et al., "The Degradation, Swelling and Erosion Properties . . . ," Biomaterials, Elsevier Science Publishers, vol. 21, No. 9, pp. 931-938, May 2000.

Gref, R., et al., "Biodegradable Long-Circulating Polymeric Nanospheres," Science, American Association for the Advancement of Science, vol. 263, pp. 1600-1603, Mar. 1994.

Ronneberger, B., et al., "In Vivo Biocompatibiilty Study of ABA Triblock . . . ," Journal of Biomedical Materials Research, vol. 30, pp. 31-40, 1996.

Morlock, M., et al., "Erythropoietin Loaded Microspheres Prepared from Biodegradable . . . ," Journal of Controlled Release, vol. 56, pp. 105-115, 1998.

Kim, K., et al., "Incorporation and Controlled Release of a Hydrophilic . . . ," Journal of Controlled Release, vol. 98, No. 1, pp. 47-56, Jul. 2004.

Zange, R., et al., "Biocompatibility Testing of ABA Triblock Copolymers Consisting . . . ," Journal of Controlled Release, vol. 56, No. 1-3, pp. 249-258, Dec. 1998.

Shin, K.C., et al., "A Facile Preparation of Highly Interconnected Macroporous PLGA . . . ," Polymer, Elsevier Science Publishers, vol. 46, No. 11, pp. 3801-3808, May 2005.

Lee, S., et al., "In Vivo Conjunctival Reconstruction Using Modified PLGA . . . ," Biomaterials, Elsevier Science Publishers, vol. 24, No. 27, pp. 5049-5059, Dec. 2003.

Mikos, A., et al., "Preparation and Characterization of . . . ," Polymer, vol. 35, No. 5, pp. 1068-1077, 1994.

* cited by examiner

DEGRADABLE HYDROPHILIC BLOCK COPOLYMERS WITH IMPROVED BIOCOMPATIBILITY FOR SOFT TISSUE REGENERATION

This is a national stage of PCT/DK07/000115 filed Mar. 7, 2007 and published in English.

FIELD OF THE INVENTION

The present invention relates to novel biodegradable polymers, to porous and other materials comprising such polymers, and to various medical uses of such materials.

BACKGROUND OF THE INVENTION

Scaffolds are porous structures into which cells may be incorporated. They are usually made up of biocompatible, degradable materials and are added to tissue to guide the organization, growth and differentiation of cells in the process of forming functional tissue. The materials used can be either of natural or synthetic origin.

Poly(L-lactide) (PLLA), poly(D/L-lactide) (PDLLA) and poly(lactide-co-glycolide) (PLGA) have been known for a long time as degradable implant materials, and they are all FDA-approved for this purpose. They have been used as scaffolds for bone, cartilage, liver, skin, urethra, intestines, tendon and cardiovascular tissues.

A typical example of one of these applications is that the polymer is made into a porous structure, often by solvent casting/particle leaching. The structure is then pre-wetted with ethanol, and washed successively with water. This step is necessary because these polymers are hydrophobic, and an attempt to wet them directly with water fails. The wet structure is then seeded with cells and grown in a bioreactor before implantation.

Copolymers of polyethers and polyesters are also known. These are usually not used as scaffolds, as PEG-containing (polyethylene glycol) polymers are known to resist adhesion of cells and proteins. This class of polymers are used as carriers in drug delivery, where the high hydrophilicity and fouling-resistance of the polyether part is useful.

PLGA and copolymers of PEG and PLGA are known to have good biocompatibility in that they are non-toxic for cells and do not invoke inflammatory response in tissue. In Zange et al., Journal of Controlled Release, 56, 1998, 249-258, the biocompatibility of various PEG-PLGA copolymers are examined with in vitro models, and none show adverse effects of the polymers on mouse fibroblasts. For a polymer to perform in a scaffold, good biocompatibility is not enough. The cells have to efficiently adhere to the material. It is known that PEG-containing polymers and PEG-coated surfaces resist adhesion of cells and proteins.

U.S. Pat. No. 6,201,072B1 teaches a group of PLGA-PEG-PLGA triblock copolymers with low molecular weight and distinct aqueous solubility characteristics for drug delivery applications.

WO 03000778 A1 uses (among other things) MPEG-PLGA (MPEG=methoxy-polyethylene glycol) with a linker in the OH-functional end for drug release purposes.

US 20040076673 discloses MPEG-PLGA with $M_w$<5000 for oral drug delivery.

CN 1446841 discloses three-dimensional porous frame materials of poly(lactide)-polyether block copolymers and a process for preparing such block copolymers.

The polymers for tissue engineering can be either natural or synthetic. The most widely used synthetic polymers are from the group of polyesters. The most common in this group are PLLA, PDLLA, PLGA, PCL (poly-ε-caprolactone), and various copolymers thereof. They are all hydrophobic materials, and initial adhesion of cells to scaffolds of these polyesters is sluggish at best.

The present inventors have found that by incorporating a hydrophilic block (i.e. a polyalkylene glycol block) in the polymer, the biocompatibility of polyesters is improved. This is due to better wetting characteristics of the material, and that initial cell adhesion is impaired on non-polar materials. Further, it has been found that by keeping the molar content of the polyalkylene units relative to the molar content of the lactide/glycolide units low, i.e. at the most 14 molar-%, superior polymers and derived materials are obtained.

BRIEF DESCRIPTION OF THE INVENTION

One aspect of the present invention relates to a biodegradable polymer of the general formula:

A-O—(CHR$^1$CHR$^2$O)$_n$—B wherein

A is a poly(lactide-co-glycolide) residue of a molecular weight of at least 4000 g/mol, the molar ratio of (i) lactide units [—CH(CH$_3$)—COO—] and (ii) glycolide units [—CH$_2$—COO—] in the poly(lactide-co-glycolide) residue being in the range of 80:20 to 10:90, in particular 70:30 to 10:90, B is either a poly(lactide-co-glycolide) residue as defined for A or is selected from the group consisting of hydrogen, C$_{1-6}$-alkyl and hydroxy protecting groups, one of R$^1$ and R$^2$ within each —(CHR$^1$CHR$^2$O)— unit is selected from hydrogen and methyl, and the other of R$^1$ and R$^2$ within the same —(CHR$^1$CHR$^2$O)— unit is hydrogen, n represents the average number of —(CHR$^1$CHR$^2$O)— units within a polymer chain and is an integer in the range of 10-1000, in particular 16-250, the molar ratio of (iii) polyalkylene glycol units [—(CHR$^1$CHR$^2$O)—] to the combined amount of (i) lactide units [—CH(CH$_3$)—COO—] and (ii) glycolide units [—CH$_2$—COO—] in the poly(lactide-co-glycolide) residue(s) is at the most 14:86, and wherein the molecular weight of the copolymer is at least 20,000 g/mol.

Another aspect of the present invention relates to a biodegradable, porous material of the general formula A-O—(CHR$^1$CHR$^2$O)$_n$—B wherein A is a poly(lactide-co-glycolide) residue of a molecular weight of at least 4000 g/mol, the molar ratio of (i) lactide units [—CH(CH$_3$)—COO—] and (ii) glycolide units [—CH$_2$—COO—] in the poly(lactide-co-glycolide) residue being in the range of 80:20 to 10:90, B is either a poly(lactide-co-glycolide) residue as defined for A or is selected from the group consisting of hydrogen, C$_{1-6}$-alkyl and hydroxy protecting groups, one of R$^1$ and R$^2$ within each —(CHR$^1$CHR$^2$O)— unit is selected from hydrogen and methyl, and the other of R$^1$ and R$^2$ within the same —(CHR$^1$CHR$^2$O)— unit is hydrogen, n represents the average number of —(CHR$^1$CHR$^2$O)— units within a polymer chain and is an integer in the range of 10-1000, the molar ratio of (iii) polyalkylene glycol units [—(CHR$^1$CHR$^2$O)—] to the combined amount of (i) lactide units [—CH(CH$_3$)—COO—] and (ii) glycolide units [—CH$_2$—COO—] in the poly(lactide-co-glycolide) residue(s) is at the most 14:86, and wherein the molecular weight of the copolymer is at least 10,000 g/mol.

wherein the porosity is at least 50%, such as in the range of 50-99.5%.

A third aspect of the present invention relates to a method for the preparation of a biodegradable, porous material of a polymer, the method comprising the steps of:
(a) dissolving a polymer as defined herein in a non-aqueous solvent so as to obtain a polymer solution;
(b) freezing the solution obtained in step (a) so as to obtain a frozen polymer solution; and
(c) freeze-drying the frozen polymer solution obtained in step (b) so as to obtain the biodegradable, porous material.

Further aspects of the present invention relates to a medical device element of a material comprising a polymer as defined herein; a medical device of a material comprising a polymer as defined herein; a biodegradable, porous material as defined herein for use in therapy, dentistry or surgery; the use of a biodegradable, porous material as defined herein for the preparation of a scaffold for supporting cell adhesion or the in-growth for regeneration of tissue; the use of a biodegradable, porous material as defined herein for the preparation of a wound dressing; and a method of supporting cell adhesion and/or the in-growth for regeneration of tissue, the method comprising the step of contacting a biodegradable, porous material as defined herein with said tissue.

DETAILED DESCRIPTION OF THE INVENTION

The present inventors have found that particularly designed biodegradable polymers have highly interesting properties which can be utilised in scaffolds for supporting cell adhesion and/or the in-growth for regeneration of tissue.

The Polymers

The novel biodegradable polymers are composed of a polyalkylene glycol residue and one or two poly(lactide-co-glycolide) residue(s).

Hence, the present invention i.a. relates to biodegradable polymer of the general formula:

A-O—(CHR$^1$CHR$^2$O)$_n$—B wherein

A is a poly(lactide-co-glycolide) residue of a molecular weight of at least 4000 g/mol, the molar ratio of (i) lactide units [—CH(CH$_3$)—COO—] and (ii) glycolide units [—CH$_2$—COO—] in the poly(lactide-co-glycolide) residue being in the range of 80:20 to 10:90, in particular 70:30 to 10:90, B is either a poly(lactide-co-glycolide) residue as defined for A or is selected from the group consisting of hydrogen, C$_{1-6}$-alkyl and hydroxy protecting groups, one of R$^1$ and R$^2$ within each —(CHR$^1$CHR$^2$O)— unit is selected from hydrogen and methyl, and the other of R$^1$ and R$^2$ within the same —(CHR$^1$CHR$^2$O)— unit is hydrogen, n represents the average number of —(CHR$^1$CHR$^2$O)— units within a polymer chain and is an integer in the range of 10-1000, in particular 16-250, the molar ratio of (iii) polyalkylene glycol units [—(CHR$^1$CHR$^2$O)—] to the combined amount of (i) lactide units [—CH(CH$_3$)—COO—] and (ii) glycolide units [—CH$_2$—COO—] in the poly(lactide-co-glycolide) residue(s) is at the most 14:86, and wherein the molecular weight of the copolymer is at least 20,000 g/mol.

Hence, the polymers can either be of the diblock-type or of the triblock-type.

It is understood that the polymer comprises either one or two residues A, i.e. poly(lactide-co-glycolide) residue(s). It is found that such residues should have a molecular weight of at least 4000 g/mol, more particularly at least 5000 g/mol, or even at least 8000 g/mol.

The poly(lactide-co-glycolide) of the polymer can be degraded under physiological conditions, e.g. in bodily fluids and in tissue. However, due to the molecular weight of these residues (and the other requirements set forth herein), it is believed that the degradation will be sufficiently slow so that materials and objects made from the polymer can fulfil their purpose before the polymer is fully degraded.

The expression "poly(lactide-co-glycolide)" encompasses a number of polymer variants, e.g. poly(random-lactide-co-glycolide), poly(DL-lactide-co-glycolide), poly(mesolactide-co-glycolide), poly(L-lactide-co-glycolide), the sequence of lactide/glycolide in the PLGA can be either random, tapered or as blocks and the lactide can be either L-lactide, DL-lactide, D-lactide, or meso-lactide.

Preferably, the poly(lactide-co-glycolide) is a poly(random-lactide-co-glycolide) or poly(tapered-lactide-co-glycolide).

Another important feature is the fact that the molar ratio of (i) lactide units [—CH(CH$_3$)—COO—] and (ii) glycolide units [—CH$_2$—COO—] in the poly(lactide-co-glycolide) residue(s) should be in the range of 80:20 to 10:90, in particular 70:30 to 10:90.

It has generally been observed that the best results are obtained for polymers wherein the molar ratio of (i) lactide units [—CH(CH$_3$)—COO—] and (ii) glycolide units [—CH$_2$—COO—] in the poly(lactide-co-glycolide) residue(s) is 70:20 or less, or 70:30 or less, however fairly good results were also observed when for polymer having a respective molar ratio of up to 80:20 as long as the molar ratio of (iii) polyalkylene glycol units [—(CHR$^1$CHR$^2$O)—] to the combined amount of (i) lactide units [—CH(CH$_3$)—COO—] and (ii) glycolide units [—CH$_2$—COO—] in the poly(lactide-co-glycolide) residue(s) was at the most 10:90.

As mentioned above, B is either a poly(lactide-co-glycolide) residue as defined for A or is selected from the group consisting of hydrogen, C$_{1-6}$-alkyl and hydroxy protecting groups.

In one embodiment, B is a poly(lactide-co-glycolide) residue as defined for A, i.e. the polymer is of the triblock-type.

In another embodiment, B is selected from the group consisting of hydrogen, C$_{1-6}$-alkyl and hydroxy protecting groups, i.e. the polymer is of the diblock-type.

Most typically (within this embodiment), B is C$_{1-6}$-alkyl, e.g. methyl, ethyl, 1-propyl, 2-propyl, 1-butyl, tert-butyl, 1-pentyl, etc., most preferably methyl. In the event where B is hydrogen, i.e. corresponding to a terminal OH group, the polymer is typically prepared using a hydroxy protecting group as B. "Hydroxy protecting groups" are groups that can be removed after the synthesis of the polymer by e.g. hydrogenolysis, hydrolysis or other suitable means without destroying the polymer, thus leaving a free hydroxyl group on the PEG-part, see, e.g. textbooks describing state-in-the-art procedures such as those described by Greene, T. W. and Wuts, P. G. M. (Protecting Groups in Organic Synthesis, third or later editions). Particularly useful examples hereof are benzyl, tetrahydropyranyl, methoxymethyl, and benzyloxycarbonyl. Such hydroxy protecting groups may be removed in order to obtain a polymer wherein B is hydrogen.

One of $R^1$ and $R^2$ within each —(CHR$^1$CHR$^2$O)— unit is selected from hydrogen and methyl, and the other of $R^1$ and $R^2$ within the same —(CHR$^1$CHR$^2$O)— unit is hydrogen. Hence, the —(CHR$^1$CHR$^2$O)$_n$— residue may either be a polyethylene glycol, a polypropylene glycol, or a poly(ethylene glycol-co-propylene glycol). Preferably, the —(CHR$^1$CHR$^2$O)$_n$— residue is a polyethylene glycol, i.e. both of $R^1$ and $R^2$ within each unit are hydrogen.

n represents the average number of —(CHR$^1$CHR$^2$O)— units within a polymer chain and is an integer in the range of 10-1000, in particular 16-250. It should be understood that n represents the average of —(CHR$^1$CHR$^2$O)— units within a pool of polymer molecules. This will be obvious for the person skilled in the art. The molecular weight of the polyalkylene glycol residue (—(CHR$^1$CHR$^2$O)$_n$—) is typically in the range of 750-10,000 g/mol, e.g. 750-5,000 g/mol.

The —(CHR$^1$CHR$^2$O)$_n$— residue is typically not degraded under physiological conditions, by may—on the other hand—be secreted unaltered from the human body.

The molar ratio of (iii) polyalkylene glycol units [—(CHR$^1$CHR$^2$O)—] to the combined amount of (i) lactide units [—CH(CH$_3$)—COO—] and (ii) glycolide units [—CH$_2$—COO—] in the poly(lactide-co-glycolide) residue(s) also plays a certain role and should be at the most 14:86. More typically, the ratio is at the most 12:88, in particular at the most 10:90, or even at the most 8:92. Often, the ratio is in the range of 0.5:99.5 to 14:86, such as in the range of 1:99 to 14:86, or in the range of 1:99 to 12:88, in particular in the range of 2:98 to 10:90, or even in the range of 2:98 to 8:92.

It is believed that the molecular weight of the copolymer for use in the porous materials is not particularly relevant as long as it is at least 10,000 g/mol. Preferably, however, the molecular weight is at least 15,000 g/mol. The "molecular weight" is to be construed as the number average molecular weight of the polymer, because the skilled person will appreciate that the molecular weight of polymer molecules within a pool of polymer molecules will be represented by values distributed around the average value, e.g. represented by a Gaussian distribution. More typically, the molecular weight is in the range of 10,000-1,000,000 g/mol, such as 15,000-250,000 g/mol, or 20,000-200,000 g/mol. Particularly interesting polymers are found to be those having a molecular weight of at least 20,000 g/mol, such as at least 30,000 g/mol.

The polymer structure may be illustrated as follows (where R is selected from hydrogen, $C_{1-6}$-alkyl and hydroxy protecting groups; n is as defined above, and m, p and ran are selected so that the above-mentioned provisions for the poly(lactide-co-glycolide) residue(s) are fulfilled):

(I)

diblock-type polymer (II)

triblock-type polymer

For each of the above-mentioned polymer structures (I) and (II) will be appreciated that the lactide and glycolide units [—CH$_2$—COO—] represented by p and m may be randomly distributed depending on the starting materials and the reaction conditions.

Also, it is appreciated that the lactide units [—CH(CH$_3$)—COO—] may be either D/L or L or D, typically D/L or L, or meso-lactide.

As mentioned above, the poly(lactide-co-glycolide) residue(s), i.e. the polyester residue(s), is/are degraded hydrolytically in physiological environments, and the polyalkylene glycol residue is secreted from, e.g., the mammalian body. The biodegradability can be assessed as outlined in the Experimentals section.

Preparation of Polymers

The polymers can in principle be prepared following principles known to the person skilled in the art.

In principle, polymer where B is not a residue A (diblock-type polymers) can be prepared as follows:

In principle, polymer where B is a residue A (triblock-type polymers) can be prepared as follows:

Unless special conditions are applied, the distribution of lactide units [—CH(CH$_3$)—COO—] and glycolide units [—CH$_2$—COO—] will be randomly distributed or tapered within each poly(lactic-co-glycolide) residue.

The synthesis of the polymers according to the invention is further illustrated in the Experimentals section.

The Materials

The polymers are useful for a wide range of materials for medical, dental and surgical use.

The material may, e.g. be a biodegradable, porous material comprising a polymer as defined herein, wherein the porosity is at least 50%, such as in the range of 50-99.5%.

The high degree of porosity can—as will be described further below—be obtained by freeze-drying, i.e. the material is preferably freeze-dried.

The void space of the material of the polymer may be unoccupied so as to allow or even facilitate cell adhesion and/or in-growth for regeneration of tissue. In one embodiment, however, the pores of the material are at least partly occupied by one or more components from the extracellular matrix. Such components may facilitate the cell adhesion and/or in-growth for regeneration of tissue. Examples of components from the extracellular matrix are chondroitin sulfate, hyaluronan, hyaluronic acid, heparin sulfate, heparan sulfate, dermatan sulfate, growth factors, thrombin, fibrin, fibronectin, elastin, collagen, gelatin, and aggrecan.

The components from the extracellular matrix could be added either as particles, which are heterogeneously dispersed, or as a surface coating. The concentration of the components from the extracellular matrix relative to the synthetic polymer is typically in the range of 0.5-15% (w/w), preferably below 10% (w/w). Moreover, the concentration of the components of the extracellular matrix is preferably at the most 0.3% (w/v), e.g. at the most 0.2 (w/v), relative to the volume of the material. In some embodiments, however, the concentration of the components from the extracellular matrix relative to the synthetic polymer may be as high as 80%, such as 40-70%. Within these embodiments, the concentration of the components of the extracellular matrix is preferably 0.1-5% (w/v), e.g. 0.5-4% (w/v).

With respect to biodegradability, it is in some embodiments preferred that the degree of degradation of the material is in the range of 0.9-0.1, such as 0.8-0.2, when tested for 28 days in the Biodegradation Test described in the Experimentals section.

The porous materials may be prepared according to known techniques, e.g. as disclosed in Antonios G. Mikos, Amy J. Thorsen, Lisa A Cherwonka, Yuan Bao & Robert Langer. Preparation and characterization of poly(L-lactide) foams. Polymer 35, 1068-1077 (1994). One very useful technique for the preparation of the porous materials is, however, freeze-drying.

Hence, the present invention also provides a method for the preparation of a biodegradable, porous material of a polymer, the method comprising the steps of:

(a) dissolving a polymer as defined herein in a non-aqueous solvent so as to obtain a polymer solution;

(b) freezing the solution obtained in step (a) so as to obtain a frozen polymer solution; and (c) freeze-drying the frozen polymer solution obtained in step (b) so as to obtain the biodegradable, porous material.

The non-aqueous solvent used in the method should with respect to melting point be selected so that it can be suitable frozen. Illustrative examples hereof are dioxane (mp. 12° C.) and dimethylcarbonate (mp. 4° C.).

In one variant, the polymer solution, after step (a) is poured or cast into a suitable mould. In this way, it is possible to obtain a three-dimensional shape of the material specifically designed for the particular application.

Moreover, the invention also encompasses a variant wherein particles of components from the extracellular matrix are dispersed in the solution obtained in step (a) before the solution (dispersion) is frozen at defined in step (b).

The invention also encompasses the more specific variant wherein the components from the extracellular matrix are dissolved in a suitable solvent and then added to the solution obtained in step (a). By mixing with the solvent of step (a), i.e. a solvent for the polymer defined herein, the components from the extracellular matrix will most likely precipitate so as to form a dispersion.

Further, the invention encompasses a variant wherein the biodegradable, porous material obtained in step (c), in a subsequent step, is immersed in a solution of glucosaminoglycan (e.g. hyaluronan) and subsequently freeze-dried again.

The invention also provides a medical device element of a material comprising a polymer as defined herein.

When used in the present context, the expression "medical device" is intended to encompass wound dressings, sutures, implants, etc. The term "element" is intended to mean a certain part, section, or layer of said medical device.

Hence, in one embodiment, the element is the outer coating of a medical device.

In another embodiment, the material forms the outer layer of a wound dressing.

In a particular variant, the invention provides a medical device of a material comprising a polymer as defined herein, i.e. the medical device is made entirely of the material. In one variant, the medical device is in the form of a mesh or net, in particular a mesh, such as a hernia mesh. In another variant, the medical device is in the form of a fibre, in particular a suture.

In some alternative embodiments, the material are present in the form of a fibre or a fibrous structure prepared from the polymer defined herein, possibly in combination with components from the extracellular matrix. Fibres or fibrous materials may be prepared by techniques known to the person skilled in the art, e.g. by melt spinning, electrospinning, extrusion, etc. Such fibres or fibrous materials may, e.g., be used as sutures, hernia-meshes, scaffolds, etc.

Various Uses

As it will be obvious from the above, the polymers and materials have a multitude of uses within the field of medicine, healthcare, surgery, dentistry, etc., in particular uses where a biodegradable polymer is required, e.g. for wound dressings, scaffolds for cell attachment and in-growth for regeneration of tissue, sutures, hernia-mesh, cartilage, ligaments, implants, etc.

Hence, the present invention also relates to a biodegradable, porous material as defined herein for use in therapy, dentistry or surgery.

More particular, the invention also relates to the use of a biodegradable, porous material as defined herein for the preparation of a scaffold for supporting cell adhesion or the in-growth for regeneration of tissue, and to the use of a biodegradable, porous material as defined herein for the preparation of a wound dressing.

The invention further relates to a method of supporting cell adhesion and/or the in-growth for regeneration of tissue, the method comprising the step of contacting a biodegradable, porous material as defined herein with said tissue, e.g. where the tissue is at least one selected from the group consisting of skin, ligament, tendon, cartilage, bone, muscle, cardiovascular tissue, and dental tissue.

EXPERIMENTALS

Biodegradation Test

Biodegradability of the porous material can be determined as follows.

Approx. 1 gram of a porous material is fully immersed in a medium (10% foetal calf serum in DMEM (Dulbecco's modified Eagle's medium)) at is store at 37° C. for a period of 28 days. The medium is changed twice a week, i.e. on days 3, 7, 10, 14, 17, 21, and 24. On day 28, the porous material is analysed by GCP. The biodegradation is measured as the number/weight average molecular weight relative to the initial value.

A porous MPEG-PLGA (2-30 kDa, L:G 50:50) was tested, and the biodegradation was determined as approx. 0.5 (final $M_{n/w}$ value relative to initial value)

Summary

As an attempt to make PLGA more hydrophilic, MPEG or PEG was copolymerised with PLGA to give copolymers with a low MPEG/PEG-content (<20% (w/w) MPEG/PEG). When these polymers were tested and compared to plain PLGA, the initial adhesions of cells to MPEG-PLGA and PLGA-PEG-PLGA were superior to plain PLGA and the morphology and attachment of the cells were better.

This is surprising, since PEG-containing polymers are known from the literature to resist the adhesion of proteins and cells. The key to the improved performance of our polymers seems to be that the PEG-content in the polymer is kept low (at the most 14 mol-%) as polymers with high PEG-content gave poor adhesion and morphology in the biological tests.

PLA have long degradation-times compared to PLGA, and our experiments show that a higher lactide content in the PLGA-part of polyether-PLGA give a slower adhesion of cells.

Known synthetic biodegradable polymers are typically hydrophobic materials with sluggish initial cell adhesion in a biological environment. We attempted to modify the hydrophilicity of PLGA by synthesizing an MPEG-PLGA block copolymer. Our first polymer was a 1.9-30 kDa MPEG-PLGA with an G:L-ratio of 50:50 (mol). These are made into thin porous sheets by freeze-drying. In a biological assay both the initial and long-term cell adhesion was excellent, and the performance was superior to the unmodified PLGA. This is surprising since the literature describes that incorporation of PEG into polymers make them resistant to the adhesion of cells and proteins. The key to our success seems to be that we have a low PEG-content (6% (w/w)) (see Table 2 below). When the PEG content is higher (MPEG-PLGA 5-30 kDa, 14% (w/w) PEG) we see a reduced cell adhesion, both initial and longer term when compared to the low-PEG materials and plain PLGA.

Purification of Reagents

DL-lactide and glycolide are recrystallized in dry ethylacetate in a nitrogen atmosphere and dried with vacuum. PEG/MPEG is dissolved in a suitable solvent, precipitated in cold hexane, filtered, and dried overnight. Stannous 2-ethylhexanoate is vacuum-distilled and stored under nitrogen. Ethyl acetate is distilled from calcium hydride under nitrogen. Dioxane is distilled from sodium/benzophenone under nitrogen. Toluene is distilled from sodium/benzophenone under nitrogen.

Synthesis of Polymers

PEG/MPEG, DL-lactide, glycolide and 4%(w/v) stannous octanoate in toluene are added to a vial in a glove box with nitrogen atmosphere. The vial is closed, heated and shaken until the contents are clear and homogeneous and then placed in an oven at 120-200° C. for 1 min to 48 hours, e.g. up to 6 h.

The synthesis can also be made in a solution in a suitable solvent (e.g. dioxane) to facilitate the subsequent purification. Then MPEG, DL-lactide, glycolide, 4% stannous 2-ethylhexanoate and 100% (w/w) dioxane are added to a vial in a glove box with nitrogen atmosphere, and treated as above.

Purification of Polymer

The polymer (see Table 1) is dissolved in a suitable solvent (e.g. dioxane, tetrahydrofuran, chloroform, acetone), and precipitated with stirring in a non-solvent (e.g. water, methanol, ethanol, 1-propanol or 2-propanol) at a temperature of −40 to 40° C. The polymer is left to settle, solvent discarded and the polymer is dried in a vacuum oven at 40-120° C./overnight.

The polymers are analyzed with NMR-spectroscopy and GPC to confirm structure, molecular weight and purity.

TABLE 1

Examples of the synthesis of various MPEG-PLGA polymers

| Polymer | G/L-ratio | glycolide (g) | DL-lactide (g) | Initiator | initiator (g) | 4% Sn(Oct)$_2$ (µL) | dioxane (g) |
|---|---|---|---|---|---|---|---|
| 750-15000 50 L | 50:50 | 2.12 | 2.64 | MPEG 750 Da | 0.238 | 129 | 5 |
| 1100-20000 50 L | 50:50 | 2.11 | 2.63 | MPEG 1100 Da | 0.261 | 98 | 5 |

TABLE 1-continued

Examples of the synthesis of various MPEG-PLGA polymers

| Polymer | G/L-ratio | glycolide (g) | DL-lactide (g) | Initiator | initiator (g) | 4% Sn(Oct)$_2$ (µL) | dioxane (g) |
|---|---|---|---|---|---|---|---|
| 1900-30000 50 L | 50:50 | 2.10 | 2.60 | MPEG 1900 Da | 0.298 | 65 | 5 |
| 1900-30000 80 L | 20:80 | 0.79 | 3.91 | MPEG 1900 Da | 0.298 | 65 | 5 |
| 5000-30000 50 L | 50:50 | 1.86 | 2.31 | MPEG 5000 Da | 0.833 | 68 | 5 |
| 15000-1900-15000 50 L | 50:50 | 2.10 | 2.60 | PEG 1900 Da | 0.298 | 65 | 5 |
| 30000-5000-30000 50 L | 50:50 | 2.06 | 2.56 | PEG 5000 Da | 0.385 | 31 | 5 |

Process for Making Scaffolds

Polymer (e.g. 1.9-30 kDa) is dissolved in a suitable solvent (e.g. dioxane) to a concentration of 0.5-10% (w/v). The solution is poured in a mold, frozen and freeze-dried to a porous sheet. Components from the extracellular matrix may be incorporated either by dispersing such components in the solvent or by subsequently treating the porous sheet with a dispersion/solution of components from the extracellular matrix.

Testing of Scaffolds

Biocompatibility studies (see Table 2) of the different scaffolds of MPEG-PLGA and PLGA were performed by seeding primary fibroblast at a concentration of $2.5 \times 10^4$ cells/cm$^2$ on the surface of the scaffolds. Evaluation of the cells attachment, viability and growth were performed at day 1, 3 and 7 by staining the cells using neutral red followed by evaluation using an Leica DMIRE2 inverted microscope fitted with a Evolution MP cooled color camera (Media Cybernetics) and digital images were taken using Image Pro Plus 5.1 software (Media Cybernetics).

Studies comparing the biocompatibility of freeze dried scaffolds of PLGA showed generally adhering of cells with fine morphology but very low initial amount of cells. Comparing these scaffolds with MPEG-PLGA 2-30 kDa, we see a better biocompatibility of the MPEG-PLGA scaffold because of a higher amount of cells are adhering to this scaffold due to a better wetting ability.

Cells are growing with a fine morphology and good adherence to MPEG-PLGA 1.9-30 kDa from the start of the test and an increase in amount of cells are seen from day 1 to day 7. Increasing the size of the MPEG part of the MPEG-PLGA to 5-30 kDa gives solely rounded cells with little or no adherence to the surface of the scaffolds giving a pronounced decreased biocompatibility and which is worsened from day 1 to day 7.

If MPEG-PLGA 2-15 kDa is tested and compared with MPEG-PLGA 2-20 kDa and MPEG-PLGA 2-30 kDa, we see an increasing attachment and viability of the fibroblasts when the size of the PLGA part was increased. This means that the 2-30 kDa had the best biocompatibility. Increasing the size from 2-15 kDa to 2-20 kDa gives the largest positive effect on the biocompatibility compared with the step from 2-20 kDa to 2-30 kDa.

Increasing the L:G ratio in MPEG-PLGA 2-20 kDa from 50:50 to 80:20 gives decreased attachment and viability of the fibroblasts.

TABLE 2

Summary of the biocompatibility tests

| Scaffold Type | size | LA %[2] | EO ratio[3] | % PEG (w/w) | Attachment Day 1 | Attachment Day 3 | Attachment Day 7 | Viability Day 1 | Viability Day 3 | Viability Day 7 |
|---|---|---|---|---|---|---|---|---|---|---|
| PLGA[1] | — | 50 | 0:100 | 0 | + | ++ | ++++ | +++ | +++ | ++++ |
| MPEG-PLGA | 2-15 | 50 | 16:84 | 12 (ref) | + | + | + | ++ | ++ | ++ |
|  | 2-15 | 60 | 17:83 | 12 (ref) | + | + | + | ++ | ++ | + |
|  | 2-15 | 80 | 17:83 | 12 (ref) | + | + | + | + | + | + |
|  | 2-20 | 50 | 13:87 | 9 | ++ | +++ | +++ | ++ | +++ | +++ |
|  | 2-20 | 60 | 13:87 | 9 | ++ | ++ | ++ | ++ | ++ | ++ |
|  | 2-20 | 80 | 14:86 | 9 | + | + | + | + | + | + |
|  | 2-30 | 50 | 9:91 | 6 | +++ | +++++ | +++++ | ++++ | +++++ | +++++ |
|  | 2-30 | 60 | 9:91 | 6 | +++ | ++++ | +++++ | ++++ | +++++ | +++++ |
|  | 2-30 | 80 | 9:91 | 6 | +++ | ++++ | ++++ | +++ | ++++ | ++++ |

TABLE 2-continued

Summary of the biocompatibility tests

| Scaffold Type | LA size | EO %[2] | % PEG ratio[3] | Attachment (w/w) Day 1 | Day 3 | Day 7 | Viability Day 1 | Day 3 | Day 7 |
|---|---|---|---|---|---|---|---|---|---|
| 5-25 | 50 | 23:77 | 17 (ref) | + | + | + | + | + | + |
| 5-30 | 50 | 20:80 | 14 (ref) | ++ | + | + | ++ | + | + |
| 5-79 | 50 | 9:91 | 6 | +++ | ++++ | +++++ | ++++ | +++++ | +++++ |

PLGA-PEG-PLGA

| | | | | | | | | | |
|---|---|---|---|---|---|---|---|---|---|
| 13-6-13 | 50 | 25:75 | 19 (ref) | + | + | + | + | + | + |
| 23-3-23 | 50 | 9:91 | 6 | +++ | +++++ | +++++ | ++++ | +++++ | +++++ |
| 47-6-47 | 50 | 9:91 | 6 | ++ | +++ | ++++ | +++ | +++ | +++++ |

[1] Alkermes MEDISORB PLGA 5050DL high I.V.
[2] LA as mol % of the PLGA part of the polymer
[3] ratio of EO-units to lactide/glycolide units.

The results are graded subjective from + to +++++ with + meaning low attachment and low viability while +++++ are excellent attachment and viability.

Figure 1:
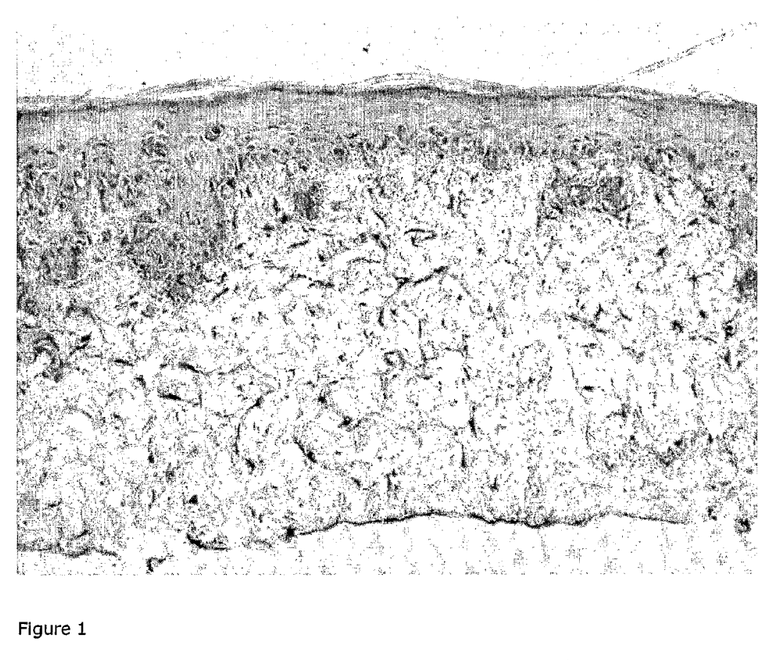
FIG. 1 illustrates MPEG-PLGA 2-30 kDa scaffolds supporting the development of reconstituted epidermis.
Figure 2:
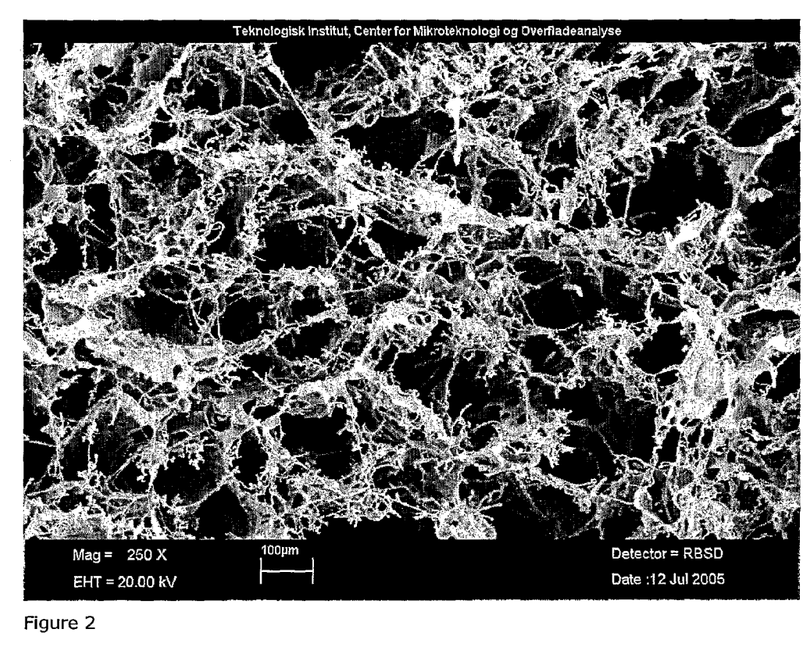
FIG. 2: 1.5% (w/w) solution of a 2-30 50% lactide polymer (6% (w/w) MPEG) in dioxane, frozen at −5° C., then freeze-dried at −20° C.
Figure 3:
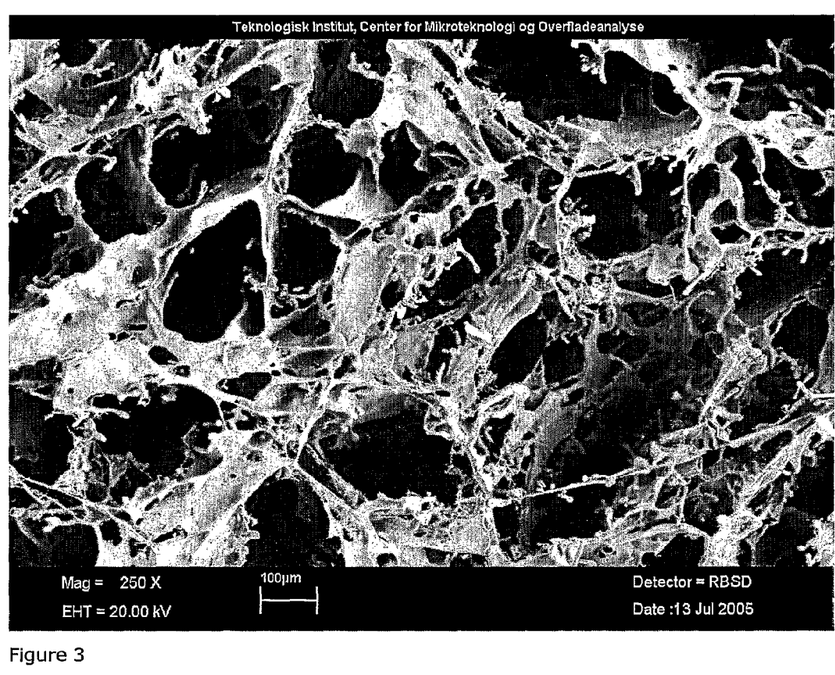
FIG. 3: 1.5% (w/w) solution of a 2-30 50% lactide polymer (6% (w/w) MPEG) in dioxane, frozen at +5° C., then freeze-dried at −20° C.

Human keratinocytes can be cultured in vitro on fibroblast populated MPEG-PLGA scaffolds to form a multilayered and differentiated reconstituted epidermis (see FIG. 1). The reconstituted epidermis shows morphological features resembling normal epidermis in vivo.

On histological specimens, we find clear evidence of basal cell layers (stratum basale) and ultimately overlying stratum corneum with intervening layers resembling, however, immature and slightly hyperproliferative, spinous and granular layers. Lack of final maturation should be ascribed to the chosen in vitro model rather than the scaffold material.

Preparation of MEPG-PLGA Scaffolds Containing ECM Particles

Preparation of composite scaffolds of MPEG-PLGA and ECM: Methoxy-polyethylene glycol-poly(lactide-co-glycolide) (Mn 2,000-30,000, L:G 1:1; prepared as described hereinabove) was dissolved in 1,4-dioxane to a 1.5% solution. For UBM (Acell Inc., USA) containing samples, the UBM was added to the solution while stirring; 0, 0.017, 0.038, 0.064, 0.1, 0.15, 0.225 g/scaffold (0, 10, 20, 30, 40, 50, 60% w/w), high-speed-mixed and 10 mL poured in 7.3×7.3 cm mould. The solution was frozen at −5° C. and lyophilized at −20° C. for 5 h and 20° C. for approx 15 h. The samples were placed in a desiccator with vacuum overnight to remove residual dioxane.

Figure 4:
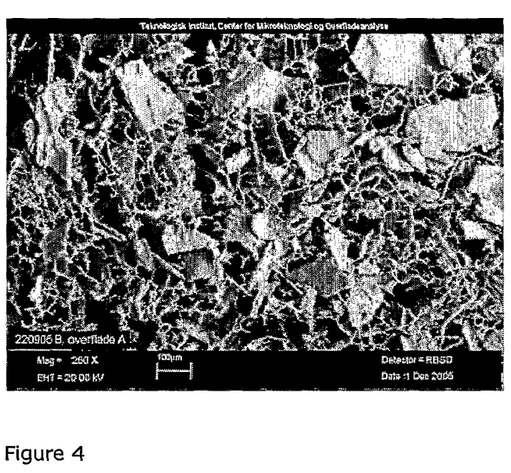
FIG. 4: SEM picture of freeze dried 1.5% MPEG-PLGA containing 40% ECM particles (magnification 250×).

SEM pictures demonstrate that the ECM particles are homogenously distributed in the scaffold matrix FIG. 4.

Preparation, Cell Morphology and 3D Growth in Composite Scaffolds of MPEG-PLGA and GAG Holding 4 Different Concentrations of GAG.

Preparation of composite scaffolds of MPEG-PLGA and glycosaminoglycans (GAG): Methoxy-polyethylene glycol-poly(lactide-co-glycolide) (Mn 2,000-30,000, L:G 1:1; prepared as described hereinabove) was dissolved in 1,4-dioxane to a 1.5% solution. For GAG containing samples, the GAG was added to the solution while stirring; 0, 0.0015, 0.0031, 0.00625, 0.013 g/scaffold (0, 1, 2, 4, 8% w/w), high-speed-mixed and 10 mL poured in 7.3×7.3 cm mould. The solution was frozen at −5° C. and lyophilized at −20° C. for 5 h and 20° C. for approx 15 h. The samples were placed in a desiccator with vacuum overnight to remove residual dioxane.

In order to evaluate the cell morphology and 3D growth of the composite scaffolds, biopsies were punched out of each type of the scaffolds and seeded with primary human fibroblasts (passage 3) on the surface of the scaffolds with a density of $2.5 \times 10^4$ cells/cm$^2$ in a small volume of growth medium (10% FCS in DMEM) containing antibiotics (penicillin, streptomycin and Amphotericin B). The scaffolds were incubated at 37° C. at 5% $CO_2$ before additional growth medium was added. Evaluation of the cells attachment, morphology, growth and population of the scaffold were preformed on day 1, 3 and 7 by staining the cells with neutral red followed by evaluation using an Leica DMIRE2 inverted microscope fitted with a Evolution MP cooled colour camera (Media Cybernetics). Digital images were taken using Image Pro Plus 5.1 software (Media Cybernetics).

The cell morphology and 3D growth in the MPEG-PLGA scaffold without GAG showed in the first days of the study adherent cells growing as a combination of rounded cells and spindle-shaped cells. The cells were growing on the surface of the scaffolds. During the rest of the study all cells became spindle-shaped and from day 3 observed growing into the scaffolds. Adding 1% (w/w) GAG into the scaffolds did not change the way the cells were growing in this study compared to MPEG-PLGA scaffold without GAG. Increasing the concentration of GAG to 2%(w/w) resulted at day 1 in cells growing more in small region where the cells were growing close together. Increasing the concentration of GAG to 4 and 8% (w/w) increased the sizes of the regions and made it difficult to distinguish separate cells.

At day 3 the cells were beginning to spread more on the surface of the scaffolds. This effect were more pronounced in 2 and 4% (w/w) compared to the scaffolds containing 8% (w/w).

Cells were at day 7 growing more on the surface of the scaffolds in the pure MPEG-PLGA scaffold and low concentration of GAG compared to more in-growth into the scaffolds containing higher concentrations of GAG and as a consequence of this cells were growing more spread with increasing concentrations of GAG.

GAG Release from Composite Scaffolds of MPEG-PLGA and GAG Holding Different Concentrations of GAG.

Preparation of composite scaffolds of MPEG-PLGA and GAG: Methoxy-polyethylene glycol-poly(lactide-co-glycolide) (Mn 2,000-30,000, L:G 1:1; prepared as described hereinabove) was dissolved in 1,4-dioxane to a 1.5% solution.

For GAG containing samples, the GAG was added to the solution while stirring; 0, 0.0015, 0.0031, 0.013 g/scaffold (0, 1, 2, 8% w/w), high-speed-mixed and 10 mL poured in 7.3× 7.3 cm mould. The solution was frozen at −5° C. and lyophilized at −20° C. for 5 h and 20° C. for approx 15 h. The samples were placed in a desiccator with vacuum overnight to remove residual dioxane.

In the dimethylmethylene blue (DMMB) assay the sulphated GAG content is measured by an increasing in OD 525 nm. The DMMB colour solution was prepared according to Farndale et al. (RW Farndale et al. Biochimica et Biophysica Acta 883:173-177, 1986). Briefly, 16 mg 1,9-dimethylmethylene blue was dissolved in 1 L of water containing 3.04 g glycine, 2.37 g NaCl and 95 mL 0.1 M HCl, pH 3.0. In order to measure the release of GAG from the MPEG-PLGA scaffolds containing 0, 1, 2 and 8% (w/w) GAG biopsies were punched out of each type of the scaffolds. These biopsies in duplicates were placed in a 48 well plate and 200 µl of DMMB solution were poured over the scaffolds corresponding to the amount necessary to cover the scaffolds. Five minutes later 100 µl of the colour solution from the wells were transferred to a 96 well plate and measured at 525 nm. A Synergy™ HT Multi-Detection Microplate Reader from Bio-Tek was used.

Figure 5:
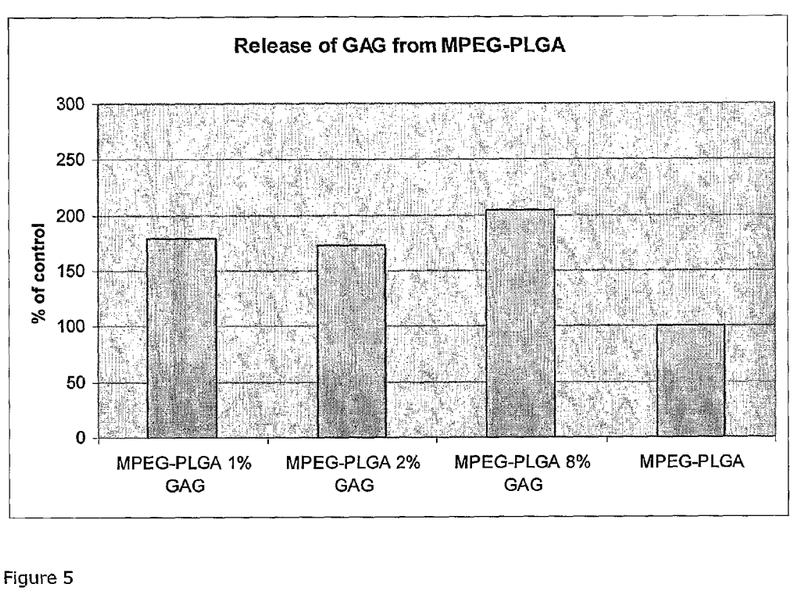
FIG. 5 illustrates the release of GAG. An immediate release of GAG from all the scaffolds containing GAG and no release from the pure MPEG-PLGA scaffold was observed. A slightly higher release was observed in the 8% scaffold compared to the 1 and 2%.

The result of the study showed an immediately release of GAG from all the scaffolds containing GAG and no release from the pure MPEG-PLGA scaffold (see FIG. 5). A slightly higher release was observed in the 8% (w/w) scaffold compared to the 1 and 2% (w/w).

Implantation of Integra and MPEG-PLGA in a 28-Day Mouse Model.

Two groups of 4 mice (NMRI mice from M&B-Taconic) at Pipeline Biotech A/S had an 8 mm biopsy of respectively Integra (Integra LifeSciences Corporation, USA) or MPEG-PLGA scaffolds (1.5% 2-30 50 L) implanted under the skin in the neck region. The skin opening was closed with sutures. At day 10 and 28, 2 mice from each group were euthanized with $CO_2$ and the area of the implantation including the surrounding area was excised and transferred to Lilly's formalin buffer before embedding in paraffin. Each paraffin block was carefully sectioned by 5 µm increments until each scaffold was located and the subsequent slices stained with haematoxylin and Eosin (H&E). Digital images were collected using a BX-60 Olympus light microscope fitted with an Evolution MP cooled colour camera (Media Cybernetics) and digital image were taken using Image Pro Plus 5.1 software. An independent pathologist performed the histopathological evaluation of the study.

The Integra showed a nice integration into the surrounding tissue and a slight fibrotic in-growth along the border of the scaffold at day 10. No fibroblasts were observed in the middle of the scaffolds. Minimal inflammation in scaffolds and surroundings, however, some giant cells were present at day 10. The scaffolds were still intact after 28 days, but without further in-growth of fibroblasts.

MPEG-PLGA showed a very nice integration into the surrounding tissue at day 10, with a mild inflammatory response and significant in-growth of fibroblast cells along the border, corresponding to a desirable fibrotic response, and migrating cells in the middle of the scaffold. In contrast to Integra, the in-growth continued at day 28 with formation of neodermis and without an inflammatory response.

In conclusion, the animal study showed that MPEG-PLGA was the best-suited scaffold material, supportive of fibroblast in-growth, formation of neodermis and well tolerated by the host.

Cartilage Regeneration with Chondrocytes in MPEG-PLGA Scaffold (in vivo Study in Goats)

The present study aims to investigate the cartilage regenerative response of a MPEG-PLGA porous scaffold combined with chondrocyte suspension in a goat femoral condyle full thickness cartilage defect model.

Methods:

10 adult goats were used for the study and the study conducted at the Research Center at Foulum, Denmark. A 6 mm circular defect was created in both medial femoral condyles. Cartilage tissue was harvested for chondrocyte culture. At secondary open surgery the defects were randomized to the following two treatment groups.

1. Empty defect (control)
2. Fibrin/chondrocyte solution in a MPEG-PLGA freeze-dried porous scaffold (4% 2-30 50 L).

Animals were followed for 4 month. Analyses: ICRS macroscopic scoring (0-12).

Mechanical test was performed to assess stiffness of regeneration tissue. Histological analyses was performed by O, Driscoll and Pinada cartilage scores and percentage filling of the defects.

Results:

The ICRS and histology scores demonstrated highly significant difference between groups. The cartilage regeneration in the MPEG-PLGA/Cell group demonstrated high defect fill and a tissue characteristic close to hyaline cartilage whereas no regeneration tissue was seen in the empty defects. Mechanical testing demonstrated no difference between treatment groups.

CONCLUSION

The MPEG-PLGA/cell construct demonstrates an extensive cartilage regenerative response with good phenotypic characteristic. As expected no regeneration was seen in the empty defects. Porous MPEG-PLGA scaffold in combination with cultured chondrocytes seem to be a good technique for cartilage tissue engineering in vivo.

The invention claimed is:

1. A biodegradable, porous material comprising a polymer of the general formula

A-O—(CHR$^1$CHR$^2$O)$_n$—B, wherein
A is a poly(lactide-co-glycolide) residue having a molecular weight of at least 4000 g/mol, wherein the molar ratio of (i) lactide units [—CH(CH$_3$)—COO—] to (ii) glycolide units [—CH$_2$—COO—] in the poly(lactide-co-glycolide) residue is 70:30 to 10:90 and wherein the molar ratio of (iii) polyalkylene glycol units [—(CHR$^1$CHR$^2$O)—] to the combined amount of (i) lactide units [—CH(CH$_3$)—COO—] and (ii) glycolide units [—CH$_2$—COO—] in the poly(lactide-co-glycolide) residue(s) is at the most 1:9 and, wherein B is either a poly(lactide-co-glycolide) residue as defined for A or is selected from the group consisting of hydrogen, C$_{1-6}$-alkyl and hydroxy protecting groups, one of R$^1$ and R$^2$ within each —(CHR$^1$CHR$^2$O)— unit is selected from hydrogen and methyl, and the other of R$^1$ and R$^2$ within the same —(CHR$^1$CHR$^2$O)— unit is hydrogen, n represents the average number of —(CHR$^1$CHR$^2$O)— units within a polymer chain and is an integer in the range of 10-1000, the number average molecular weight of the polymer is at least 10,000 g/mol, and
wherein the porosity of the material is at least 50%.

2. The material of claim 1, wherein
B is methyl,
n is an integer in the range of 16-250, and
the number average molecular weight of the polymer is at least 20,000 g/mol.

3. The material of claim 1 in freeze-dried form.

4. The material of claim 1, wherein the pores of the material are at least partly occupied by one or more components from an extracellular matrix.

5. The material of claim 4, wherein the one or more components is selected from the group consisting of chondroitin sulfate, hyaluronan, hyaluronic acid, heparin sulfate, heparan sulfate, dermatan sulfate, growth factors, thrombin, fibrin, fibronectin, elastin, collagen, gelatin, and aggrecan.

6. A method for preparing the biodegradable, porous material of claim 1 comprising the steps of
   a) dissolving a polymer in a non-aqueous solvent so as to obtain a polymer solution, the polymer having the general formula $A\text{—}O\text{—}(CHR^1CHR^2O)_n\text{—}B$, wherein
      A is a poly(lactide-co-glycolide) residue of a molecular weight of at least 4000 g/mol, wherein the molar ratio of (i) lactide units [—CH(CH$_3$)—COO—] to (ii) glycolide units [—CH$_2$—COO—] in the poly(lactide-co-glycolide) residue is 70:30 to 10:90 and
      wherein the molar ratio of (iii) polyalkylene glycol units [—(CHR$^1$CHR$^2$O)—] to the combined amount of (i) lactide units [—CH(CH$_3$)—COO—] and (ii) glycolide units [—CH$_2$—COO—] in the poly(lactide-co-glycolide) residue(s) is at the most 1:9 and,
      wherein B is either a poly(lactide-co-glycolide) residue as defined for A or is selected from the group consisting of hydrogen, C$_{1-6}$-alkyl and hydroxy protecting groups,
      one of R$^1$ and R$^2$ within each —(CHR$^1$CHR$^2$O)— unit is selected from hydrogen and methyl, and the other of R$^1$ and R$^2$ within the same —(CHR$^1$CHR$^2$O)— unit is hydrogen,
      n represents the average number of —(CHR$^1$CHR$^2$O)— units within a polymer chain and is an integer in the range of 10-1000, and
      the number average molecular weight of the polymer is at least 10,000 g/mol,
   b) freezing the polymer solution so as to obtain a frozen polymer solution, and
   c) freeze-drying the frozen polymer solution so as to obtain the biodegradable, porous, material.

7. A method of supporting cell adhesion or cell in-growth for regeneration of a tissue comprising the step of contacting the biodegradable, porous material of claim 1 with the tissue.

8. A scaffold, for supporting cell adhesion or cell in-growth for regeneration of tissue, comprising the biodegradable, porous material of claim 1.

9. A scaffold, for supporting cell adhesion or cell in-growth for regeneration of tissue, comprising the biodegradable, porous material of claim 2.

10. A wound dressing comprising the biodegradable, porous material of claim 1.

11. A wound dressing comprising the biodegradable, porous material of claim 2.

12. An element, useful in a medical device, comprising the biodegradable, porous material of claim 1.

13. A medical device comprising the element of claim 12.

* * * * *